United States Patent
Aichinger et al.

(10) Patent No.: US 6,187,947 B1
(45) Date of Patent: *Feb. 13, 2001

(54) METHOD FOR PRODUCING (METH) ACRYLIC ACID ESTERS

(75) Inventors: Heinrich Aichinger, Mannheim; Michael Fried, Heidelberg; Gerhard Nestler, Ludwigshafen, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 09/308,252

(22) PCT Filed: Nov. 21, 1997

(86) PCT No.: PCT/EP97/06512

§ 371 Date: May 25, 1999

§ 102(e) Date: May 25, 1999

(87) PCT Pub. No.: WO98/23578

PCT Pub. Date: Jun. 4, 1998

(30) Foreign Application Priority Data

Nov. 25, 1996 (DE) .............................. 196 48 743

(51) Int. Cl.⁷ .......................... C07C 67/08; C07C 67/58; C07C 69/54
(52) U.S. Cl. ........................................... 560/205; 560/218
(58) Field of Search ...................................... 560/205, 218

(56) References Cited

U.S. PATENT DOCUMENTS

| | | |
|---|---|---|
| 2,917,538 | 12/1959 | Carlyle . |
| 4,280,010 * | 7/1981 | Erpenbach et al. ................... 560/205 |
| 4,698,440 * | 10/1987 | Blair et al. ........................... 560/205 |
| 5,093,520 * | 3/1992 | Nestler et al. ....................... 560/218 |
| 5,386,052 | 1/1995 | Sakakura . |
| 5,510,514 | 4/1996 | Fauconet et al. . |

FOREIGN PATENT DOCUMENTS

| | | |
|---|---|---|
| 551111 | 7/1993 | (EP) . |
| 0 566 047 | 10/1993 | (EP) . |
| 0 609 127 | 1/1994 | (EP) . |
| 0618187 | 10/1994 | (EP) . |
| 1120284 | 7/1968 | (GB) . |

OTHER PUBLICATIONS

Chemical Abstract, AN 163589n, vol. 92, 1980, CZ 179,808, Jul. 15, 1979.

Kirk–Othmer, Encyclopedia of Chem. Technol., vol. 1, pp. 347–348. date not available.

* cited by examiner

*Primary Examiner*—Gary Geist
*Assistant Examiner*—Leigh C. Maier
(74) *Attorney, Agent, or Firm*—Oblon, Spivak, McClelland, Maier & Neustadt, P.C.

(57) ABSTRACT

The disclosure is a process for preparing (meth)acrylic esters by reacting (meth)acrylic acid with $C_4$–$C_6$-alkanols in the presence of a strong inorganic acid or of a $C_4$–$C_6$-monoalkyl ester of a polybasic strong acid as catalyst, which comprises removing the unconverted alkanol from the resulting reaction mixture by distillation and thereafter removing the catalyst from the resulting mixture.

17 Claims, No Drawings

METHOD FOR PRODUCING (METH) ACRYLIC ACID ESTERS

BACKGROUND OF THE INVENTION

Field of the Invention

The present invention relates to a process for preparing esters of acrylic or methacrylic acid [(meth)acrylic acid]. (Meth)acrylic esters are generally produced in industry by esterification of (meth)acrylic acid with alkanols in the presence of strong acids as esterification catalysts (e.g. sulfuric acid, phosphoric acid, alkanesulfonic acids, arylsulfonic acids or cation exchangers having sulfonic acid groups). Such processes are known for example from Kirk-Othmer, Encyclopedia of Chemical Technology, Vol. 1, pages 347–348.

As well as the desired ester and optionally an entrainer, the esterification mixture also includes unconverted starting materials (alkanol, (meth)acrylic acid) and the catalyst and also the corresponding alkyl acetate and dialkyl ether as low boiling by-products. The alkyl acetate is formed from the acetic acid which is always formed as a by-product in the synthesis of acrylic acid by propylene oxidation or from acetylene by the Reppe process, and is very difficult to separate from the acrylic acid, as known for example from EP-A 551 111 and GB-B-1 120 284. It is well known that ethers are formed from alkanols in the presence of strong acids.

The esterification mixture is generally worked up in multiple stages:
1. Extraction of the catalyst with water (known from EP-A-618 187) and/or neutralization with an aqueous base (known from EP-A-566 047 and EP-A-609 127).
2. Wash with water and alkanol removal (known from EP-A-566 047, col. 1, 1. 19–21).
3. Distillative removal of low boilers (e.g. acetate, ether, unconverted alkanol) and any entrainer used (known from U.S. Pat. No. 2 917 538, col. 1, 1. 61–68).
4. Distillative removal of (meth)acrylate from high boilers (e.g. oligomers, polymers, Michael addition products, polymerization inhibitors).

However, the processes recited under 1 and 2 in particular have the following disadvantages:

The acids used as catalysts, and any of their esters which are formed, have to be removed from the reaction mixture before further processing. Generally, this is accomplished by washing and neutralizing the reaction mixture with alkali or alkaline earth metal hydroxide or carbonate solutions. The resulting wastewaters are difficult to dispose of benignly. If sulfuric acid is used as catalyst, it will react with the alkanol in question to form chiefly its monoester, as mentioned. The salts of sulfuric monoesters, especially the salts of the esters with higher alkanols, are surface-active and would, on disposal, appreciably impair the quality of t he wastewaters from the process and cause a considerable loss of product of value.

Furthermore, direct neutralization gives rise to a layer of sludge, which greatly impairs the separation between ester phase and water phase (EP-A-566 047, col. 1, 1. 49ff). A very complicated neutralization with bases of different strengths is proposed to solve this problem (ibidem).

Recovery of the catalyst is thus desirable for ecological and economic reasons. Appropriate processes are known. For instance, CZ-B-179 808 discloses a process for recovering mineral acids from esterification mixtures by extracting the esterification mixture with water, concentrating the aqueous phase by distillation and recycling the resulting concentrated aqueous catalyst solution into the esterification reaction. However, this process is energy-intensive.

EP-A-0 618 187 (= U.S. Pat. No. 5,386,052) describes a process for preparing (meth)acrylic esters by extracting the catalyst with water and recycling the extract into the esterification reaction, optionally after distillative concentration. However, it is emphasized that sulfuric acid is not suitable for use as catalyst by reason of the poor extractability of the monoalkyl sulfate, since the large amount of water which would be necessary to ensure adequate extraction of the monoalkyl sulfate would affect the esterification reaction adversely. The catalyst used is therefore selected from alkyl- or aryl-sulfonic acids (column 2, line 55ff), which, however, are significantly more expensive than sulfuric acid.

Following catalyst removal or neutralization of the acids, the esterification mixture is saturated with water (1 to 2% by weight, based on the esterification mixture). Before extraction or neutralization, the esterification mixture contains only about 0.1% by weight of water, based on the reaction mixture. However, the economically desirable isolation of the alkanol for recycling into the esterification process cannot take the form of a simple distillative removal of the alkanol from this water-saturated mixture owing to the formation of binary and ternary azeotropes. Such azeotropes are illustrated below in Table 1 for butanol.

TABLE 1

| Azeotrope | % by weight, based on azeotropic mixture | bp. at 1 bar |
|---|---|---|
| water/butanol/butyl acetate | 27.7%/10.7%/61.6% | 89.9° C. |
| water/butyl acetate | 27.3%/72.7%/ | 90.3° C. |
| water/butanol/butyl ether | 29.9%/27.8%/42.3% | 90.4° C. |
| water/butanol/butyl acrylate | 39.5%/28.9%/31.6% | 92.9° C. |
| water/butyl ether | 33.9%/66.1% | 93.1° C. |
| water/butanol | 48.0%/52.0% | 93.5° C. |
| water/butyl acrylate | 39.7%/60.3% | 94.4° C. |

A direct recycle of the butanol fraction would thus always also mean having to recycle water, which would have an unfavorable effect on the esterification equilibrium. In addition, the alkyl acetate or dialkyl ether formed would also be recycled, which would lead to an undesirable continuous enrichment of this ester or ether in the esterification mixture.

An elaborate distillative separation of water, alkanol, acetic ester, ether and target ester is therefore required to prevent losses of products of value.

In addition, owing to the relatively good water solubility of some of the alkanols (e.g. butanol, about 7% at 20° C.), considerable amounts of unconverted alkanols will also always be extracted with water in the course of the neutralization of the remaining acids and/or the subsequent wash. This makes it necessary to provide an additional workup for the aqueous phase (by stripping, for example) to recover the alkanols.

SUMMARY OF THE INVENTION

It is an object of the present invention to develop a technically simple and economical process for preparing (meth)acrylic esters whereby unconverted alkanol can be recovered from the esterification reaction mixture by simple distillative isolation. In addition, the alkanol fraction shall be directly recyclable into the esterification.

DETAILED DESCRIPTION OF THE REFERRED EMBODIMENTS

We have found that, surprisingly, the alkanol is distillable out of the reaction mixture without the presence of the strongly acidic esterification catalyst during the distillation giving rise to acid-catalyzed secondary reactions such as, for example, ether or olefin formation or addition of the alkanol to the double bond of the (meth)acrylate (Michael addition).

The present invention accordingly provides a process for preparing (meth)acrylic esters by reacting (meth)acrylic acid with $C_4$–$C_6$-alkanols in the presence of a strong inorganic acid or of a monoester of a polybasic strong inorganic acid as catalyst, which comprises removing the unconverted alkanol from the reaction mixture by distillation and thereafter removing the catalyst from the resulting mixture.

The esterification is essentially carried out in a conventional manner, i.e. by reacting (meth)acrylic acid with a $C_4$–$C_6$-alkanol in the presence of a catalyst and at elevated temperature. The molar ratio of alkanol:acrylic or methacrylic acid is generally within the range from 1:0.7 to 1:1.2. $C_4$–$C_6$-Alkanols include for example pentanol, hexanol and also, preferably, butanols, especially n-butanol. The catalyst concentration in the reaction mixture is generally within the range from 0.1 to 10% by weight, preferably within the range from 0.5 to 5% by weight, based on the total batch. The catalyst used is preferably sulfuric acid or the corresponding mono-$C_4$–$C_6$-alkyl sulfate.

The polymerization inhibitors used include for example phenothiazine, hydroquinone, hydroquinone monomethyl ether or mixtures thereof and optionally air (from 0.1 to 10 1/h×1) in an amount from 100 to 5000 ppm, based on the reaction mixture. The process of the invention can be carried out with entrainers to remove water from the reaction mixture selected from saturated hydrocarbons (e.g. cyclohexane) or aromatics (e.g. toluene); preferably, however, the reaction is carried out without additional entrainer.

The reaction temperature is generally within the range from about 70 to 160° C., preferably within the range from 90 to 130° C.

The reaction time is generally within the range from about 1 to 10, preferably from 1 to 6, hours.

The reaction can be carried out under atmospheric, reduced or superatmospheric pressure. The pressure is preferably set so that the water formed during the esterification is distilled off, for example in the form of a mixture of water, $C_4$–$C_6$-alkanol and ester (the organic components being recycled into the esterification).

The esterification can be carried out continuously or batchwise, the continuous reaction procedure being preferred.

The esterification is carried out in customary apparatus, for example in an esterification unit composed of one or more heatable stirred reactors (battery) which are optionally equipped with columns, condensers and phase separation vessels. The reactor contents are mixed by stirring or other customary suitable measures.

The post-esterification reaction mixture is substantially freed from any alkanol in a conventional distillation apparatus (e.g. column with sieve plates, Raschig rings, ordered packing elements, etc.). The distillation also removes some of the $C_4$–$C_6$-alkyl acetate formed during the esterification and the di-$C_4$–$C_6$-alkyl ether.

The distillation conditions depend on the type of alkanol used and are preferably chosen so that not more than 50% of ether or acetate are found in the distillate. Typical distillation conditions include for example for n-butanol a base of column temperature from 80 to 150° C., a pressure from 200 to 1000 mbar and a reflux ratio from 2:1 to 8:1.

The distillate (5–15% of the feed) is generally 60–80% of n-butanol, 2–4% of n-butyl acetate, 1–3% of di-n-butyl ether and 2–4% of water.

Only 10–50% of the acetate and ether formed during the esterification end up in the distillate, which is thus easy to recycle back into the esterification.

The alkanol is preferably distilled off down to a level of residual alkanol in the reaction mixture which ensures trouble-free extraction of the catalyst (sulfuric acid or the corresponding monoalkyl ester) with water. More particularly, the residual alkanol content is ≦5% by weight, preferably ≦3% by weight, particularly preferably ≦1% by weight, based on the reaction mixture.

In a particularly preferred embodiment, the recovered alkanol is recycled back into the esterification directly.

The catalyst is preferably removed from the reaction mixture by extraction with water.

When using sulfuric acid as catalyst, it was surprisingly found that the alkanol content has a considerable influence on the extractability of the monoalkyl sulfate, which likewise acts as an esterification catalyst (see Table 1). After distillative removal of the alkanol according to the invention, the catalyst can be extracted with small amounts of water, so that the extract can be recycled back into the esterification. The conditions for the extraction of the catalyst from the esterification mixture are preferably chosen so that the catalyst concentration in the aqueous phase is not less than 20% by weight, especially not less than 25% by weight, based on the aqueous extract, and the degree of extraction is not less than 70%, especially not less than 80%.

To achieve this, the extraction is carried out with from about 5 to 20% by weight of water, especially from about 6 to 15% by weight of water, based on the total weight of the mixture to be extracted. The resulting extract can be recycled back into the esterification directly, without having to be concentrated.

The extraction can be carried out in a conventional manner. It is preferably carried out countercurrently, for example in columns without energy input, pulsed columns, columns with rotating internals, mixer-settler apparatus or in static mixers.

The extraction can be carried out at ambient temperature or higher temperatures, but is advantageously carried out at a temperature within the range from about 15 to 40° C.

If, thereafter, there is still a need for an extraction/neutralization of the remaining acids (catalyst and (meth)acrylic acid) with the aid of an aqueous base, this can take place in a conventional extraction apparatus (see above), in which case the base requirements will be low because of the high degree of extraction of the catalyst and the extraction will proceed without the phase separation problems described in EP-A-0 566 074.

The ester is isolated from the reaction mixture which has been freed from catalyst and optionally residual carboxylic acid and low boilers, in a conventional manner, especially distillatively, for example by distillation in a sieve plate column.

The Example which follows illustrates the invention. Percentages are by weight. "Butanol" and "butyl" are n-butanol and n-butyl, respectively.

A stirred tank battery consisting of 3 stirred reactors which each have a reaction volume of 1l and are collectively equipped with a column, a condenser and a phase separation vessel is charged with 500 g of acrylic acid, 547 g of n-butanol, 12.3 g of sulfuric acid and 1 g of phenothiazine per hour. The reaction temperature in the reactors is respectively 105° C., 118° C. and 121° C., and the pressure is 700 mbar. The mixture obtained at the top of the column is a mixture of water, n-butanol and n-butyl acrylate, and it separates into an aqueous and an organic phase, and the organic phase is returned into the column as reflux.

The reactor effluent contains according to gas-chromatographic analysis:

87.6% of butyl acrylate,
4.5% of butanol,
0.3% of butyl acetate,
0.5% of dibutyl ether.

The water content is 0.1%.

This esterification mixture is fed onto the midpoint plate of a 55 sieve plate column for a continuous distillation at a base of column temperature of 121° C. (440 mbar) and a top of column temperature of 85° C. (300 mbar) using a reflux ratio of 3.5 and a distillate removal amounting to 6% of the feed.

The distillate contains according to gas-chromatographic analysis:

64.7% of butanol,
28.1% of butyl acrylate,
30 1.9% of butyl acetate,
1.9% of dibutyl ether, and is recycled back into the esterification directly.

The recycle rate is about 40% for the acetate and about 25% for the ether, and the butanol recovery rate is about 85%.

The distillation bottom product which, as well as butyl acrylate, additionally contains (according to analysis)

0.7% of butanol,
40 0.2% of butyl acetate,
0.4% of dibutyl ether,
2.11% of monobutyl sulfate, is cooled down to 30° C. and treated with 6% of water in a mixer-settler apparatus. The recovered aqueous phase contains 24.6% of monobutyl sulfate and is recycled back into the esterification directly. The degree of extraction is 87%.

The organic phase, which still contains 0.8% of acrylic acid and 0.25% of butyl sulfate, is treated with 6% strength aqueous sodium hydroxide solution (5% based on organic phase) in a mixer-settler apparatus.

The aqueous phase obtained only contains 0.3% of butanol in addition to the corresponding sodium salts, and is disposed of.

The recovered substantially acid-free organic phase (acrylic acid content <100 ppm) is stripped in a 60 sieve plate column of the low boilers (chiefly acetate and ether). The base of column temperature is 110° C., the top of column temperature is 88° C. at 160 mbar, and the reflux ratio is 7, with 10% of the feed being removed as distillate.

The bottom product is subjected to a distillation in a further sieve plate column (30 plates) to recover the butyl acrylate (base of column temperature 108° C., top of column temperature 80° C. at 100 mbar, reflux ratio 0.6).

The dependence of the degree of catalyst extraction on the butanol content of the reaction mixture subjected to extraction was determined by subjecting esterification mixtures which were obtained from an esterification of an acrylic acid with butanol in the presence of sulfuric acid, and which differed in butanol content, to a single extraction with 10% of water in a separating funnel at 25° C. The results of these experiments are shown in Table 2.

TABLE 2

| Butanol content | 0.1% | 2.5% | 5.0% | 10% |
|---|---|---|---|---|
| Cat. content | 1.93% | 1.88% | 1.83% | 1.75% |
| Degree of extraction | 89% | 88% | 71% | 55% |
| Residual cat. content | 0.22% | 0.23% | 0.53% | 0.97% |

It can be seen that the degree of extraction increases with decreasing butanol content.

We claim:

1. A process for preparing (meth)acrylic esters comprising
   reacting (meth)acrylic acid with $C_4$–$C_6$-alkanols in the presence of a strong inorganic acid or of a $C_4$–$C_6$-monoalkyl ester of a polybasic strong inorganic acid as catalyst,
   removing the unconverted alkanol from the reaction mixture by distillation and recycling it directly back into the reaction;
   and thereafter
   removing the catalyst from the resulting mixture by extraction with water and recycling the so-formed aqueous solution of the catalyst back into the esterification.

2. The process of claim 1, wherein the distillative removal of the unconverted alkanol is effected to a level of residual alkanol in the reaction mixture of less than 3% by weight, based on the reaction mixture.

3. The process of claim 2, wherein the level of residual alkanol is less than 5% by weight.

4. The process of claim 1, wherein the alkanol is n-butanol.

5. The process of claim 1, wherein the catalyst is sulfuric acid or a monoalkyl sulfate.

6. The process of claim 1, wherein the extraction of the catalyst is carried out in such a way that the catalyst concentration in the aqueous phase is not less than 20% by weight, based on the aqueous extract.

7. The process of claim 6, wherein the catalyst concentration in the aqueous phase is not less than 25% by weight.

8. The process of claim 1, wherein the extraction of the catalyst is carried out in such a way that the degree of extraction is not less than 80% by weight, based on the catalyst quantity in the reaction mixture.

9. The process of claim 1, wherein the extraction is carried out at from 15 to 40° C.

10. The process of claim 1, wherein the extraction is carried out countercurrently or in a static mixer.

11. The process of claim 1, wherein the reaction temperature is within the range from 70 to 160° C.

12. The process of claim 11, wherein the reaction temperature is from 90 to 130° C.

13. The process of claim 11, wherein the reaction time is within the range from 1 to 1 0 hours.

14. The process of claim 13, wherein the reaction time is from 1 to 6 hours.

15. The process of claim 11, which is continuous.

16. The process of claim 1, wherein said inorganic acid is sulfuric acid.

17. The process of claim 1, wherein the $C_4$–$C_6$-monoalkyl ester of a polybasic inorganic acid is a $C_4$–$C_6$-monoalkyl ester of sulfuric acid.

* * * * *

UNITED STATES PATENT AND TRADEMARK OFFICE
CERTIFICATE OF CORRECTION

PATENT NO.    : 6,187,947 B1
DATED         : February 13, 2001
INVENTOR(S)   : Heinrich Aichinger et al.

It is certified that error appears in the above-identified patent and that said Letters Patent is hereby corrected as shown below:

<u>Column 6,</u>
Line 29, "than 3% by weight," should read -- than 5% by weight, --;
Line 32, "than 5% by weight." should read -- than 3% by weight. --;
Line 55, "claim 11," should read -- claim 1, --;
Line 56, "from 1 to 1 0 hours." should read -- from 1 to 10 hours. --;
Line 59, "claim 11," should read -- claim 1, --.

Signed and Sealed this

Sixteenth Day of April, 2002

Attest:

JAMES E. ROGAN
*Attesting Officer*   *Director of the United States Patent and Trademark Office*